(12) United States Patent
Sugita

(10) Patent No.: US 8,469,946 B2
(45) Date of Patent: Jun. 25, 2013

(54) OPERATION UNIT AND TREATMENT TOOL FOR ENDOSCOPE PROVIDED WITH THE SAME

(75) Inventor: Noriyuki Sugita, Saitama (JP)

(73) Assignee: Hoya Corporation, Tokyo (JP)

( * ) Notice: Subject to any disclaimer, the term of this patent is extended or adjusted under 35 U.S.C. 154(b) by 1097 days.

(21) Appl. No.: 12/429,389

(22) Filed: Apr. 24, 2009

(65) Prior Publication Data

US 2009/0281375 A1    Nov. 12, 2009

(30) Foreign Application Priority Data

May 9, 2008   (JP) ................................. 2008-122831

(51) Int. Cl.
*A61B 17/00* (2006.01)

(52) U.S. Cl.
USPC .............................................. 606/1; 600/564

(58) Field of Classification Search
USPC ........................... 606/1, 44–46, 174; 600/564
See application file for complete search history.

(56) References Cited

U.S. PATENT DOCUMENTS

| | | | | |
|---|---|---|---|---|
| 5,425,745 A | * | 6/1995 | Green et al. | 606/219 |
| 5,849,022 A | * | 12/1998 | Sakashita et al. | 606/174 |
| 7,674,262 B2 | * | 3/2010 | Sugita et al. | 606/45 |
| 2004/0172018 A1 | | 9/2004 | Okada | |
| 2007/0282336 A1 | | 12/2007 | Kawano | |
| 2008/0033237 A1 | | 2/2008 | Ouchi | |
| 2008/0077130 A1 | | 3/2008 | Shibata et al. | |
| 2008/0114353 A1 | | 5/2008 | Sugita et al. | |
| 2008/0319263 A1 | | 12/2008 | Maruyama | |

FOREIGN PATENT DOCUMENTS

| | | |
|---|---|---|
| JP | 61-018885 | 6/1986 |
| JP | 2004-261372 | 9/2004 |

* cited by examiner

*Primary Examiner* — Victor Nguyen

(74) *Attorney, Agent, or Firm* — Greenblum & Bernstein P.L.C.

(57) ABSTRACT

An operation unit of a treatment tool for an endoscope includes a first joining member configured to be joined to a rear end of a flexible sheath of the treatment tool, a second joining member configured such that the first joining member is fitted therearound rotatably around an axis line of the first joining member relative to the second joining member, and a pin fit hole formed between the first joining member and the second joining member such that a pin is fitted therein, the pin fit hole being configured to restrict rotational movement of the first joining member around the axis line relative to the second joining member when the pin is fitted in the pin fit hole.

9 Claims, 6 Drawing Sheets even when the first joining member is fitted around the second joining member so as to restrict movement of the first joining member in a direction along the first axis line relative to the second joining member.

OPERATION UNIT AND TREATMENT TOOL FOR ENDOSCOPE PROVIDED WITH THE SAME

BACKGROUND OF THE INVENTION

The following description relates to one or more operation units of a treatment tool for an endoscope.

An operation unit of a treatment tool for an endoscope is in general configured such that a wire operating member is provided slidably relative to an operation unit body. Here, the wire operating member is configured to move an operation wire back and forth in a flexible sheath in the axis line direction of the operation wire, from the rear end of the operation unit, (for example, see Japanese Patent Provisional Publication No. 2004-261372).

In addition, there is a type of treatment tool having a conveniently improved operation unit which is configured such that a flexible sheath is joined to an operation unit body rotatably around the axis line of the flexible sheath (for example, see Japanese Utility Model Provisional Publication No. SHO61-18885).

SUMMARY OF THE INVENTION

There are various types of treatment tools for an endoscope. Thus, in order to reduce production costs of the treatment tools, the treatment tools are manufactured with a common operation unit attached thereto.

Additionally, it is considered to achieve a further cost reduction by putting, into a common configuration, an operation unit adapted such that a flexible sheath is joined rotatably to an operation unit body and an operation unit adapted such that a flexible sheath is joined to an operation unit body in an un-rotatable manner.

As one of possible techniques to attain a common configuration between the operation units, for instance, a technique is considered in which a rotatable portion, of the operation unit adapted such that the flexible sheath is joined rotatably to the operation unit body, is fixed with bonding material so as to be employed for the operation unit with the flexible sheath joined to the operation unit body in an un-rotatable manner.

However, in order to fix the rotatable portion with the bonding material, not only a process to apply the bonding material but also a process to dry the bonding material is required. It results in a serious increase in a total production cost (for example, a cost increase by several tens of yen up to more than a hundred yen). Furthermore, it is difficult to visually distinguish the operation unit with the rotatable portion fixed with the bonding material from the operation unit with the rotatable portion not fixed. Therefore, a lot of efforts are required for management to prevent the operation units from being mistakenly used.

Aspects of the present invention are advantageous to provide one or more improved operation units of treatment tools for an endoscope that can easily be used commonly for both types of a flexible sheath joined rotatably to an operation unit body and a flexible sheath joined to an operation unit body in an un-rotatable manner, with little expense and concern about misuse of the operation units.

According to aspects of the present invention, an operation unit of a treatment tool for an endoscope is provided, which includes a first joining member configured to be joined to a rear end of a flexible sheath of the treatment tool, a second joining member configured such that the first joining member is fitted therearound rotatably around a first axis line of the first joining member relative to the second joining member, and a pin fit hole formed between the first joining member and the second joining member such that a pin is fitted therein, the pin fit hole being configured to restrict rotational movement of the first joining member around the first axis line relative to the second joining member when the pin is fitted in the pin fit hole.

Optionally, the first joining member may be fitted around the second joining member so as to restrict movement of the first joining member in a direction along the first axis line relative to the second joining member.

Further optionally, the operation unit may further include a circumferential groove formed circumferentially on an outer surface of the second joining member to be recessed from the outer surface, and a projection formed on an inner surface of the first joining member to protrude from the inner surface, the projection being configured to engage with the circumferential groove when the first joining member is fitted around the second joining member.

Optionally, the operation unit may further include the pin fitted in the pin fit hole.

Yet optionally, the operation unit may further include a gap formed between the first joining member and the second joining member such that the pin fitted in the pin fit hole is externally visible through the gap.

Still optionally, the pin may be a spring pin.

Optionally, the pin fit hole may be formed to extend in a direction parallel to the first axis line of the first joining member and a second axis line of the second joining member.

Optionally, the operation unit may further include a first groove formed on the inner surface of the first joining member, and a second groove formed on the outer surface of the second joining member. In this case, the first groove and the second groove may be configured to form the pin fit hole therebetween when the first joining member is fitted around the second joining member.

Further optionally, the second groove may be formed within an area on the outer surface of the second joining member, the area being covered with the first joining member.

According to aspects of the present invention, further provided is a treatment tool for an endoscope that includes an operation unit. The operation unit includes a first joining member configured to be joined to a rear end of a flexible sheath of the treatment tool, a second joining member configured such that the first joining member is fitted therearound rotatably around an axis line of the first joining member relative to the second joining member, and a pin fit hole formed between the first joining member and the second joining member such that a pin is fitted therein, the pin fit hole being configured to restrict rotational movement of the first joining member around the axis line relative to the second joining member when the pin is fitted in the pin fit hole.

BRIEF DESCRIPTION OF THE ACCOMPANYING DRAWINGS

DETAILED DESCRIPTION OF THE EMBODIMENTS

It is noted that various connections are set forth between elements in the following description. It is noted that these connections in general and, unless specified otherwise, may be direct or indirect and that this specification is not intended to be limiting in this respect.

Figure 2:
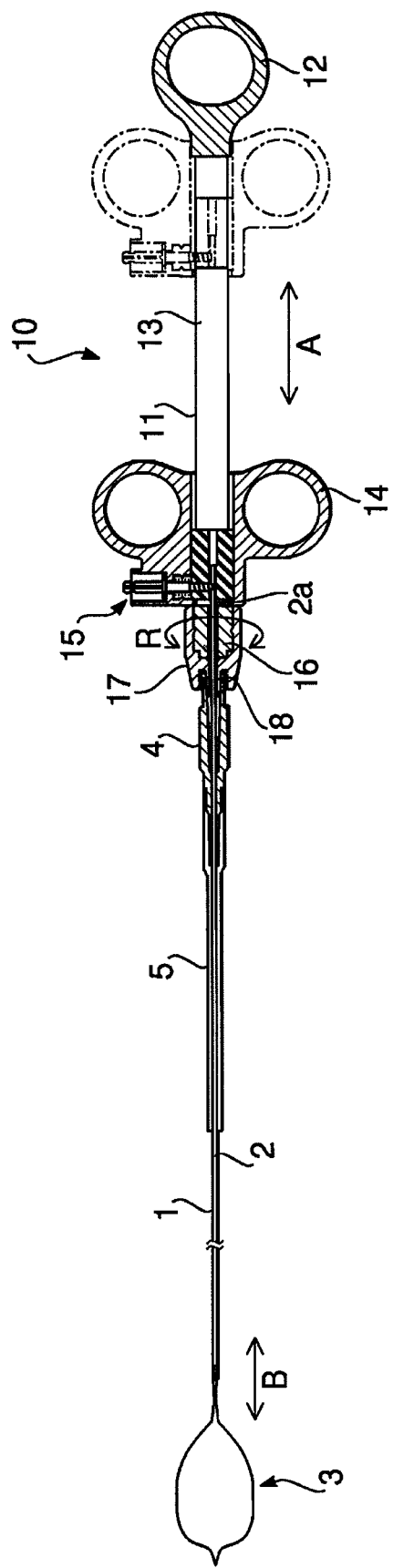
FIG. 2 is a cross-sectional side view showing an entire configuration of a high frequency snare for an endoscope to which the operation unit is applied in the embodiment according to one or more aspects of the present invention.

Hereinafter, an embodiment according to aspects of the present invention will be described with reference to the accompanying drawings. FIG. 2 shows a high frequency snare as one of treatment tools for an endoscope. A flexible sheath 1 is configured to be inserted into and pulled out of a treatment tool insertion channel (not shown) of an endoscope. In the flexible sheath 1, an electrically conductive operation wire 2 is inserted so as to move back and forth in the direction along the axis line of the flexible sheath 1 and to rotate around the axis line. Further, a snare loop as a distal end treatment member 3 is joined to the distal end of the operation wire 2 so as to protrude and recede from the distal end of the flexible sheath 1.

A sheath base sleeve 4, fixedly attached to the base end (rear end) of the flexible sheath 1, is formed in a shape of a lure-lock male fitting. A portion of the flexible sheath 1 near the rear end of the flexible sheath 1 is covered with a bending-resistant tube 5 to prevent the portion of the flexible sheath 1 from being bent and broken.

An operation unit 10 of the treatment tool for an endoscope includes an operation unit body 11 formed in an elongated shape from plastic material. The operation unit body 11 has a finger hook 12 which is formed at the rear end of the operation unit body 11 such that an operator hitches his first finger thereto.

In addition, the operation unit body 11 includes a slit 13 formed in a shape elongated in the longitudinal direction of the operation unit body 11. A wire operating member 14, which is configured to move the operation wire 2 back and forth from the rear end of the operation unit 10, is slidably engaged with the slit 13. The wire operating member 14 has a finger hook formed such that the second and third fingers of the operator are hitched thereto.

Additionally, the wire operating member 14 includes a connector 15 configured to be connected with a high frequency power code (not shown). The distal end of electrode of the connector 15 presses a rear end portion 2a of the operation wire 2 against the wire operating member 14 such that the rear end portion 2a is fixed to the wire operating member 14.

Consequently, when the wire operating member 14 is operated to move back and forth in the longitudinal direction of the operation unit body 11 as indicated by an arrow A, the operation wire 2 is moved back and forth in the flexible sheath 1 in the axis line direction of the flexible sheath 1. Then, as indicated by an arrow B, the distal end treatment member 3 is moved back and forth so as to protrude and recede from the distal end of the flexible sheath 1. Thus, a high frequency current is supplied to the distal end treatment member 3 via the operation wire 2.

A sheath joining ring 17 (i.e., a first joining member) made of plastic material is configured to be joined fixedly to and separated from the sheath base sleeve 4. The sheath joining ring 17 includes a distal end half portion as a lure-lock female fitting 18 which is formed such that the sheath base sleeve 4 is engaged therewith and disengaged therefrom. Further, the sheath joining ring 17 includes a rear end half portion formed in a cylindrical shape with a knurled concave-convex outer surface. However, in this respect, the sheath joining ring 17 may be attached to the rear end of the flexible sheath 1 in a completely fixed manner.

The operation unit body 11 includes a joining ring fit portion 16 (i.e., a second joining member) which is formed at the leading edge thereof such that the rear end half portion of the sheath joining ring 17 is fitted around the joining ring fit portion 16 so as to rotate around the axis line thereof. It is noted that through holes through which the operation wire 2 passes are formed on the respective axis lines of the joining ring fit portion 16 and the sheath joining ring 17.

Figure 3:
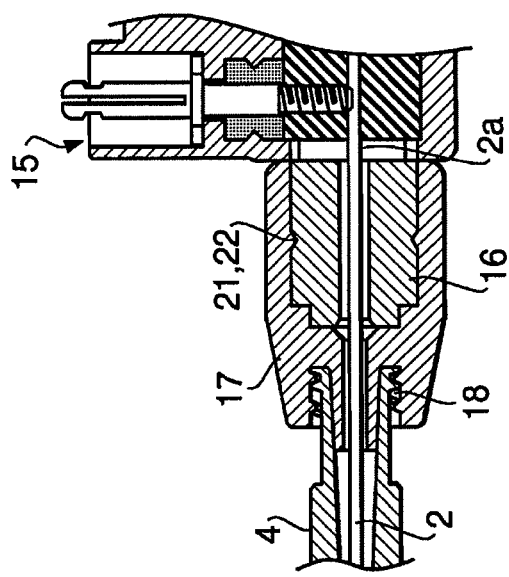
FIG. 3 is a cross-sectional side view showing a joint between a flexible sheath and the operation unit in the embodiment according to one or more aspects of the present invention.

The sheath joining ring 17 is fitted around the joining ring fit portion 16 in a manner rotatable around the axis line thereof, as indicated by an arrow R. It is noted that as illustrated in FIG. 3 in an enlarged fashion, the sheath joining ring 17 is fitted around the joining ring fit portion 16 in the state where the movement of the sheath joining ring 17 in the axis line thereof is restricted by a circumferential groove 21 and projections 22. The circumferential groove 21 is formed circumferentially on the outer surface of the joining ring fit portion 16 to be recessed from the outer surface. The projections 22 are formed circumferentially on the inner surface of the sheath joining ring 17 to protrude from the inner surface. Moreover, the circumferential groove 21 and the projections 22 are configured to engage with each other.

Figure 4:
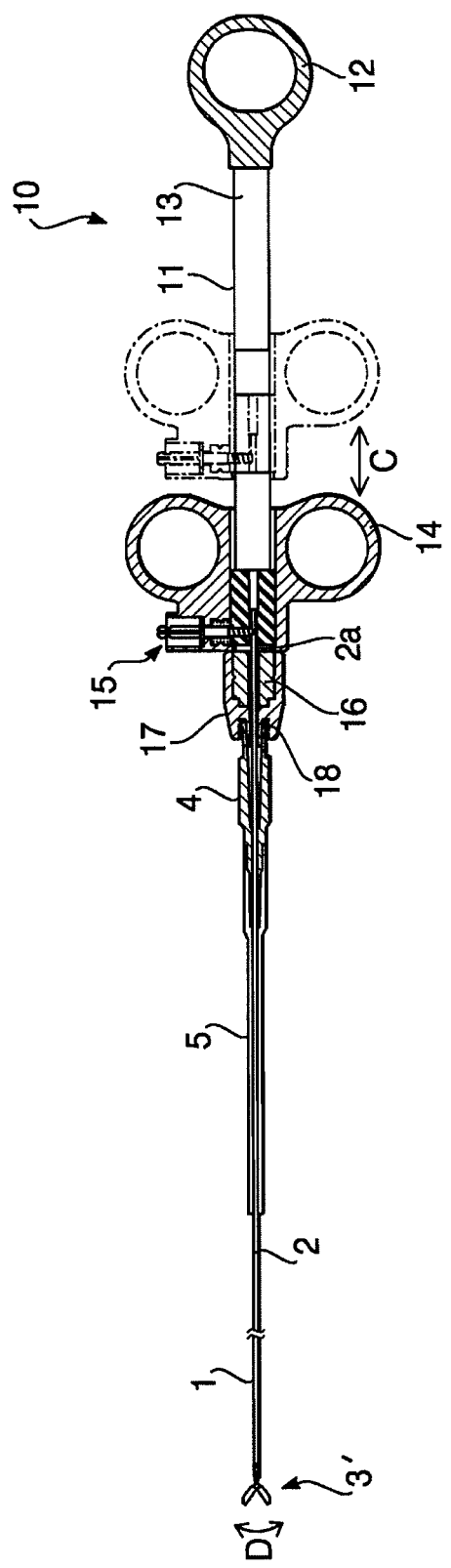
FIG. 4 is a cross-sectional side view showing an entire configuration of a beak-shaped high frequency cutting tool for an endoscope to which the operation unit is applied in the embodiment according to one or more aspects of the present invention.

FIG. 4 illustrates a beak-shaped high frequency cutting tool as one of the treatment tools for an endoscope. A pair of beak-shaped electrodes as a distal end treatment member 3' is provided at the leading edge of the flexible sheath 1 and configured to be openable and closable. By moving back and forth the wire operating member 14 as indicated by an arrow C, the operation wire 2 is moved back and forth in the flexible sheath 1, and the distal end treatment member 3' is opened and closed like a beak as indicated by an arrow D. It is noted that unlike the high frequency snare, the high frequency cutting tool is configured such that the distal end of the flexible sheath 1 and the distal end of the operation wire 2 rotate together around the axis lines thereof.

An operation unit 10 is configured in the same manner as that of the high frequency snare shown in FIG. 2. However, if a flexible sheath 1 were configured to freely rotate around the axis line thereof relative to an operation unit body 11, an operation wire 2 would have been twisted. Therefore, in this case, a sheath joining ring 17 is attached to a joining ring fit portion 16 of the operation unit body 11 so as not to rotate around the axis line thereof. The operation unit 10 of the beak-shaped high frequency cutting tool is different in the above respect from that of the high frequency snare. The different configuration therebetween will be described in detail later.

Figure 5:
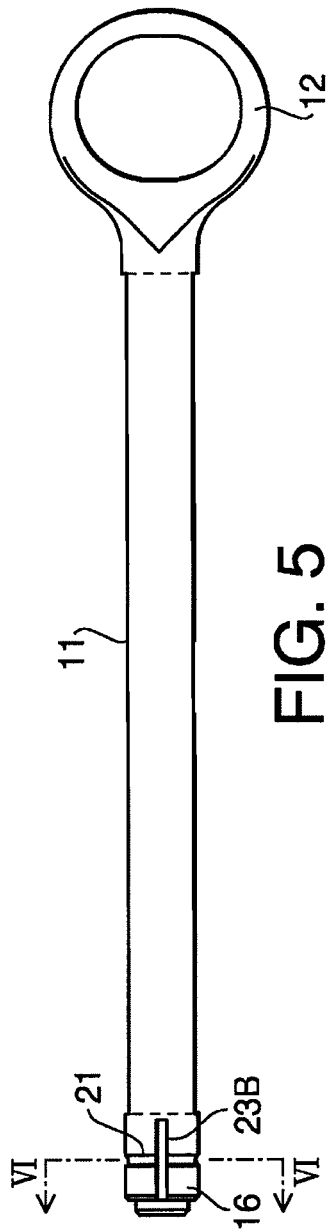
FIG. 5 is a side view of an operation unit body in the embodiment according to one or more aspects of the present invention.
Figure 6:
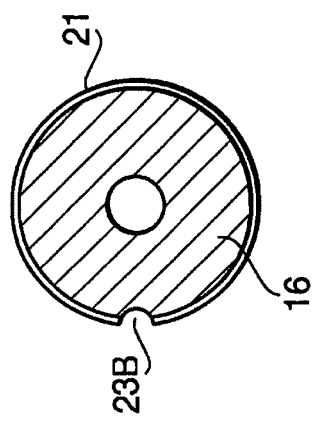
FIG. 6 is a cross-sectional view of the operation unit body along a line VI-VI shown in FIG. 5 in the embodiment according to one or more aspects of the present invention.
Figure 7:
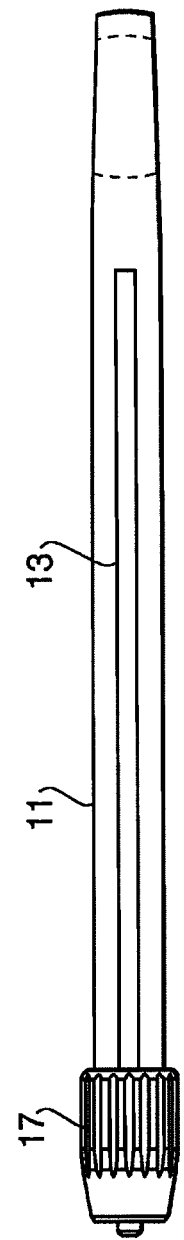
FIG. 7 is a side view showing a sheath joining ring attached to the operation unit body in the embodiment according to one or more aspects of the present invention.
Figure 8:
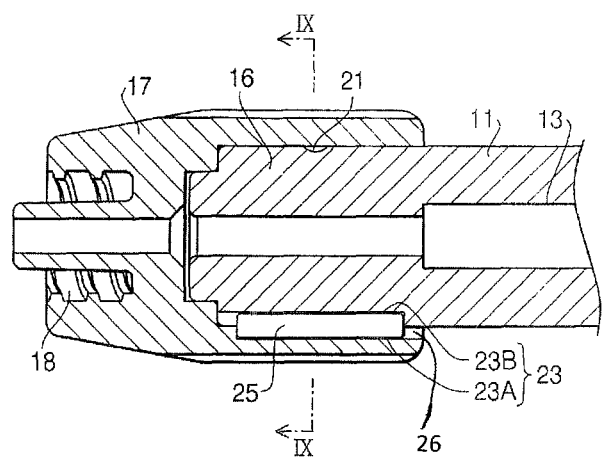
FIG. 8 is a cross-sectional side view showing an enlarged portion of the sheath joining ring attached to the operation unit body in the embodiment according to one or more aspects of the present invention.
Figure 9:
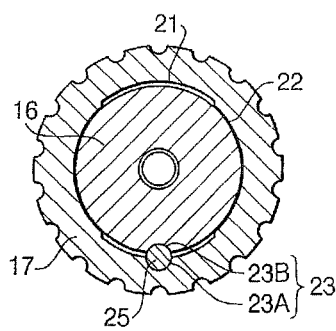
FIG. 9 is a cross-sectional view of the sheath joining ring attached to the operation unit body along a line IX-IX shown in FIG. 8 in the embodiment according to one or more aspects of the present invention.
Figure 10:
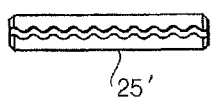
FIG. 10 is a side view of a spring pin to be used for the operation unit in the embodiment according to one or more aspects of the present invention.

FIG. 5 is a side view of the operation unit body 11 employed for both the high frequency snare and the beak-shaped high frequency cutting tool. FIG. 6 is a cross-sectional view of the operation unit body 11 along a line IV-IV shown in FIG. 5. FIG. 7 is a side view of the operation unit body 11 with the sheath joining ring 17 attached to the distal end thereof. FIG. 8 is a cross-sectional side view showing an enlarged portion of the operation unit body 11 with the sheath joining ring 17 attached to the distal end thereof as illustrated in FIG. 7. FIG. 9 is a cross-sectional view of the operation unit body 11 with the sheath joining ring 17 attached to the distal end thereof along a line IX-IX shown in FIG. 8.

As illustrated in FIGS. 5 and 6, the joining ring fit portion 16 of the operation unit body 11 includes the circumferential groove 21 formed at a middle portion in the axis line direction thereof to be recessed over the entire circumference thereof. As illustrated in FIG. 9, the projections 22 formed to protrude inward from the inner circumferential surface of the sheath joining ring 17, which is fitted around the outer circumferential surface of the joining ring fit portion 16, is engaged with the circumferential groove 21 of the joining ring fit portion 16.

Consequently, the sheath joining ring 17 is attached to the joining ring fit portion 16 of the operation unit body 11 so as to rotate around the axis line thereof yet not to move in the axis line direction thereof. It is noted that as shown in FIG. 9, the projections 22 are formed not over the entire circumference of the inner surface of the sheath joining ring 17 but separately in 180 degrees symmetry positions. Hence, in an assembling process, the sheath joining ring 17 can be fitted around the joining ring fit portion 16 by elastically deforming the sheath joining ring 17 made of plastic material.

As illustrated in FIGS. 8 and 9, a pin fit hole 23 is formed on a fit surface that is a boundary area between the sheath joining ring 17 and the joining ring fit portion 16. Additionally, the pin fit hole 23 is formed to extend in the direction parallel to the respective axis lines of sheath joining ring 17 and the joining ring fit portion 16. The pin fit hole 23 has a round cross section formed to extend into both sides of sheath joining ring 17 and the joining ring fit portion 16.

The pin fit hole 23 is formed with a joining-ring-side groove 23A and a fit-portion-side groove 23B. The joining-ring-side groove 23A is formed on the inner surface of the sheath joining ring 17 to be recessed from the fit surface between the sheath joining ring 17 and the joining ring fit portion 16. Further, the fit-portion-side groove 23B is formed on the outer surface of the joining ring fit portion 16 to be recessed from the fit surface.

When the operation unit 10 is used for the beak-shaped high frequency cutting tool, as illustrated in FIGS. 8 and 9, a hard pin 25 is firmly fitted in the pin fit hole 23 between the joining-ring-side groove 23A and the fit-portion-side groove 23B. Thereby, the sheath joining ring 17 is set not to be rotatable around the axis line thereof relative to the joining ring fit portion 16.

Meanwhile, when the operation unit 10 is used for the high frequency snare, the sheath joining ring 17 is fitted around the joining ring fit portion 16 without the pin 25 fitted in the pin fit hole 23. Consequently, the sheath joining ring 17 is set to be rotatable around the axis line thereof relative to the joining ring fit portion 16.

Figure 1:
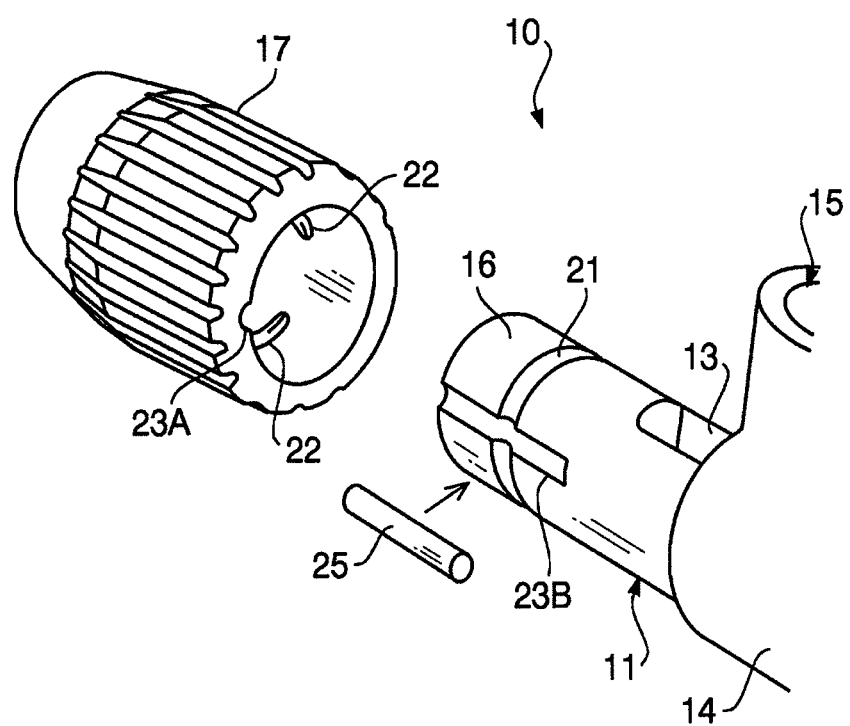
FIG. 1 is an exploded perspective view partially showing an operation unit in an embodiment according to one or more aspects of the present invention.

FIG. 1 shows a structural relationship among the sheath joining ring 17, the joining ring fit portion 16, and the pin 25 in an easily understandable manner. When the operation unit 10 is used for the beak-shaped high frequency cutting tool, the sheath joining ring 17 is fitted around the joining ring fit portion 16 with the pin 25 engaged with the fit-portion-side groove 23B. At this time, by engaging the projections 22 with the circumferential groove 21 in the state where a half portion of the pin 25 that protrudes from the fit-portion-side groove 23B is engaged with the joining-ring-side groove 23A, the sheath joining ring 17 is attached fixedly around the axis line thereof and in the axis line direction thereof, relative to the joining ring fit portion 16.

When the operation unit 10 is used for the high frequency snare, without the pin 25 engaged with the fit-portion-side groove 23B, the sheath joining ring 17 is attached to the joining ring fit portion 16, and the projections 22 are engaged with the circumferential groove 21. Thereby, the sheath joining ring 17 is attached rotatably around the axis line thereof yet fixedly in the axis line direction thereof, relative to the joining ring fit portion 16.

Thus, depending on whether the pin 25 of an inexpensive component cost (e.g., one yen) is fitted in the pin fit hole 23, the common operation unit 10 can easily be applied, with low production costs, to either a treatment tool with the flexible sheath 1 rotatably joined to the operation unit body 11 or a treatment tool with the flexible sheath 1 fixedly joined to the operation unit body 11.

As illustrated in FIG. 8, since the fit-portion-side groove 23B is formed in an area to be covered with the sheath joining ring 17, the pin 25 engaged with the fit-portion-side groove 23B is set not to touch an outside thing, and thus there are few possibilities that the pin 25 is detached in use. It is noted that when a spring pin 25', as the pin 25, is tightly fitted in the pin fit hole 23, there are less possibilities that the pin 25 (spring pin 25') is detached in use.

Further, as illustrated in FIG. 8, when the pin 25 fitted in the pin fit hole 23 is adapted to be visible externally through a gap 26 between a rear end of the sheath joining ring 17 and an outer circumferential portion of the operation unit body 11, it can be determined by the external appearance whether the pin 25 is attached to the operation unit 10. Therefore, it can easily be determined whether the operation unit 10 is intended to a treatment tool with the flexible sheath 1 rotatably joined to the operation unit body 11 or a treatment tool with the flexible sheath 1 fixedly joined to the operation unit body 11.

Furthermore, by applying coating material for improving visibility to both end faces of the pin 25, it is more easily determined whether the pin 25 is attached to the operation unit 10. In this case, when fluorescent paint or luminous paint is employed as the coating material, it is possible to certainly prevent the operation unit 10 from being mistakenly used.

Hereinabove, the embodiment according to aspects of the present invention has been described. The present invention can be practiced by employing conventional materials, methodology and equipment. Accordingly, the details of such materials, equipment and methodology are not set forth herein in detail. In the previous descriptions, numerous specific details are set forth, such as specific materials, structures, processes, etc., in order to provide a thorough understanding of the present invention. However, it should be recognized that the present invention can be practiced without reapportioning to the details specifically set forth. In other instances, well known processing structures have not been described in detail, in order not to unnecessarily obscure the present invention.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

The present disclosure relates to the subject matter contained in Japanese Patent Application No. P2008-122831, filed on May 9, 2008, which is expressly incorporated herein by reference in its entirety.

What is claimed is:

1. An operation unit of a treatment tool for an endoscope, comprising:
   a first joining member configured to be joined to a rear end of a flexible sheath of the treatment tool;
   an operation unit body;
   a second joining member, which is formed on the operation unit body, configured such that the first joining member is fitted therearound rotatably around a first axis line of the first joining member relative to the second joining member; and
   a pin fit hole formed between the first joining member and the second joining member such that a pin is fitted therein, the pin fit hole being configured to restrict rotational movement of the flexible sheath around the first axis line relative to the operation unit body, by restricting rotational movement of the first joining member around the first axis line relative to the second joining member by fitting the pin in the pin fit hole.

2. The operation unit according to claim 1, wherein the first joining member is fitted around the second joining member so as to restrict movement of the first joining member in a direction along the first axis line relative to the second joining member.

3. The operation unit according to claim 2, further comprising: a circumferential groove formed circumferentially on an outer surface of the second joining member to be recessed from the outer surface; and a projection formed on an inner surface of the first joining member to protrude from the inner surface, the projection being configured to engage with the circumferential groove when the first joining member is fitted around the second joining member.

4. The operation unit according to claim 1, further comprising the pin fitted in the pin fit hole.

5. The operation unit according to claim 4, further comprising a gap formed between the first joining member and the second joining member such that the pin fitted in the pin fit hole is externally visible through the gap.

6. The operation unit according to claim 4, wherein the pin is a spring pin.

7. The operation unit according to claim 1, wherein the pin fit hole is formed to extend in a direction parallel to the first axis line of the first joining member and a second axis line of the second joining member.

8. The operation unit according to claim 1, further comprising: a first groove formed on the inner surface of the first joining member; and a second groove formed on the outer surface of the second joining member, wherein the first groove and the second groove are configured to form the pin fit hole therebetween when the first joining member is fitted around the second joining member.

9. The operation unit according to claim 8, wherein the second groove is formed within an area on the outer surface of the second joining member, the area being covered with the first joining member.

* * * * *